United States Patent
Souza

(10) Patent No.: US 11,932,868 B2
(45) Date of Patent: *Mar. 19, 2024

(54) MICROPLATES FOR MAGNETIC 3D CULTURE

(71) Applicant: Greiner Bio-One North America, Inc., Monroe, NC (US)

(72) Inventor: Glauco Souza, Houston, TX (US)

(73) Assignee: GREINER BIO-ONE NORTH AMERICA

(*) Notice: Subject to any disclaimer, the term of this patent is extended or adjusted under 35 U.S.C. 154(b) by 133 days.

This patent is subject to a terminal disclaimer.

(21) Appl. No.: 17/176,188

(22) Filed: Feb. 16, 2021

(65) Prior Publication Data

US 2021/0163881 A1 Jun. 3, 2021

Related U.S. Application Data

(60) Division of application No. 14/965,702, filed on Dec. 10, 2015, now abandoned, which is a (Continued)

(51) Int. Cl.
*C12M 1/00* (2006.01)
*B01L 3/00* (2006.01)
(Continued)

(52) U.S. Cl.
CPC ........ *C12N 5/0062* (2013.01); *B01L 3/50853* (2013.01); *C12M 23/10* (2013.01);
(Continued)

(58) Field of Classification Search
CPC ... C12N 5/0062; C12N 13/00; B01L 3/50853; B01L 2300/046; B01L 2300/0803; B01L 2300/0829; B01L 2400/043; C12M 23/10; C12M 23/12; C12M 23/38; C12M 33/00; C12M 33/04; C12M 35/06; C12M 47/04
See application file for complete search history.

(56) References Cited

U.S. PATENT DOCUMENTS 6,100,045 A * 8/2000 Van Es ............ G01N 33/54326
435/7.1
6,294,342 B1* 9/2001 Rohr ................ G01N 33/54333
435/7.1
(Continued)

FOREIGN PATENT DOCUMENTS

WO 2004035217 A1 4/2004
WO WO2013019212 2/2013

OTHER PUBLICATIONS

Souza, G. R. et al. Three-dimensional tissue culture based on magnetic cell levitation. Nat. Nanotechnol. 5, 291-6 (2010).
(Continued)

*Primary Examiner* — Liban M Hassan
(74) *Attorney, Agent, or Firm* — BOULWARE & VALOIR, PLLC

(57) ABSTRACT

Devices for magnetic 3d culture are described including magnetic lids/bases for single Petri plates and adjustable height cap for same. Similar devices for multi-magnet culture plates wherein multiwell plates have all adjacent magnets orientated in the opposite polarity, and methods of making same.

10 Claims, 13 Drawing Sheets

Related U.S. Application Data continuation-in-part of application No. 14/331,377, filed on Jul. 15, 2014, now Pat. No. 9,909,116, and a continuation-in-part of application No. 13/762,103, filed on Feb. 7, 2013, now Pat. No. 10,407,660, which is a continuation of application No. PCT/US2011/046183, filed on Aug. 2, 2011, said application No. 14/965,702 is a continuation-in-part of application No. 13/070,873, filed on Mar. 24, 2011, now Pat. No. 8,815,231, which is a continuation of application No. PCT/US2009/058473, filed on Sep. 29, 2009.

(60) Provisional application No. 61/372,164, filed on Aug. 10, 2010, provisional application No. 61/099,966, filed on Sep. 25, 2008.

(51) Int. Cl.
  *C12M 1/22* (2006.01)
  *C12M 1/26* (2006.01)
  *C12M 1/32* (2006.01)
  *C12M 1/42* (2006.01)
  *C12N 5/00* (2006.01)
  *C12N 13/00* (2006.01)

(52) U.S. Cl.
  CPC ............ *C12M 23/12* (2013.01); *C12M 23/38* (2013.01); *C12M 33/00* (2013.01); *C12M 33/04* (2013.01); *C12M 35/06* (2013.01); *C12M 47/04* (2013.01); *C12N 13/00* (2013.01); *B01L 2300/046* (2013.01); *B01L 2300/0803* (2013.01); *B01L 2300/0829* (2013.01); *B01L 2400/043* (2013.01)

(56) References Cited

U.S. PATENT DOCUMENTS

| | | | |
|---|---|---|---|
| 6,596,162 B2 * | 7/2003 | Tuunanen | B03C 1/284 422/561 |
| 8,815,231 B2 | 8/2014 | Souza et al. | |
| 8,883,471 B2 | 11/2014 | Souza | |
| 9,688,955 B2 | 6/2017 | Souza | |
| 9,909,116 B2 | 3/2018 | Souza et al. | |
| 2006/0110296 A1 * | 5/2006 | Tajima | G01N 35/025 422/63 |
| 2006/0252054 A1 * | 11/2006 | Lin | A61B 5/150755 435/7.23 |
| 2008/0083291 A1 | 4/2008 | Krueger | |
| 2009/0137026 A1 | 5/2009 | Kobayashi et al. | |

OTHER PUBLICATIONS

Tseng, H. et al. Assembly of a three-dimensional multitype bronchiole coculture model using magnetic levitation. Tissue Eng. Part C. Methods 19, 665-75 (2013).

Tseng, H. et al. A three-dimensional co-culture model of the aortic valve using magnetic levitation. Acta Biomater. 10, 173-82 (2014).

Timm, D. M. et al. A high-throughput three-dimensional cell migration assay for toxicity screening with mobile device-based macroscopic image analysis. Sci. Rep. 3, 3000 (2013).

* cited by examiner

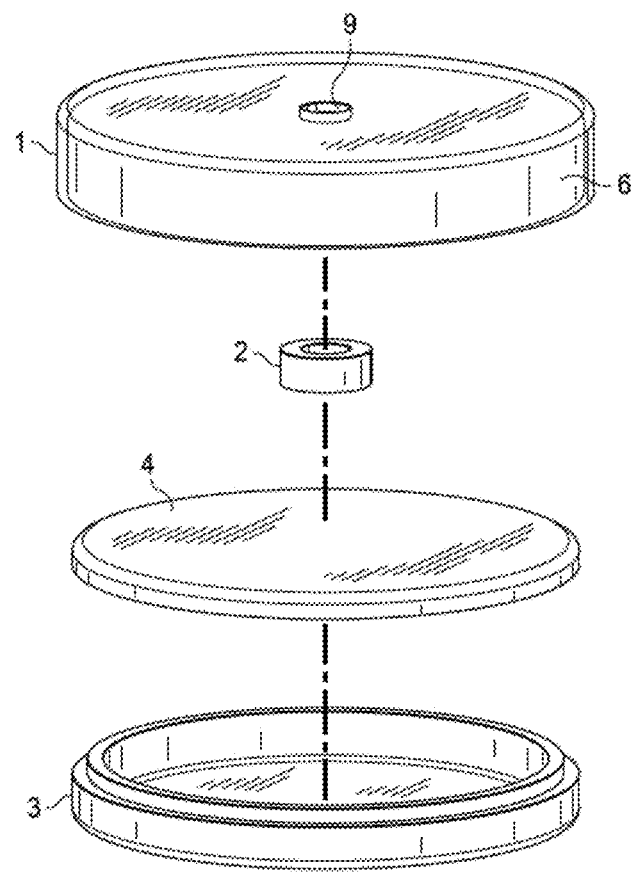
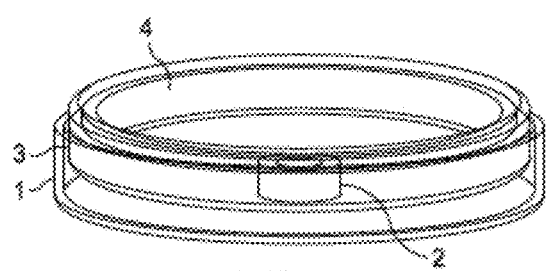
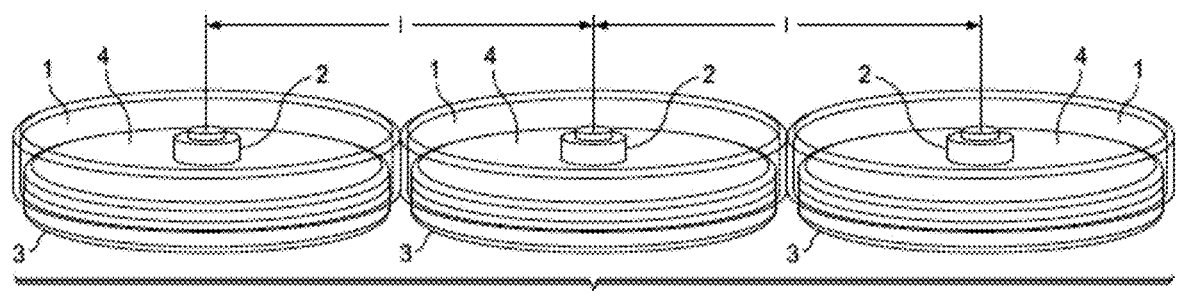
FIG. 1A
FIG. 1B
FIG. 1C

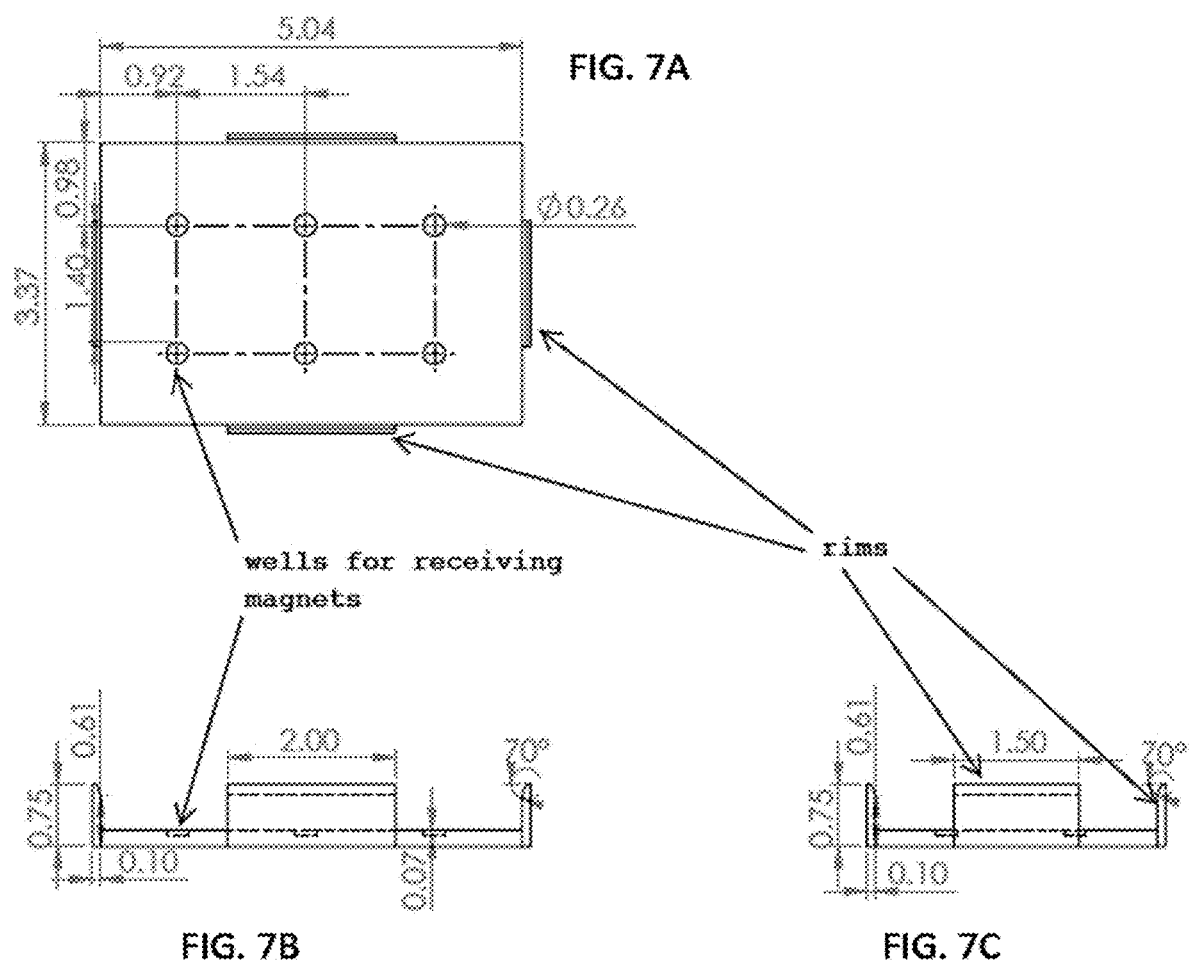

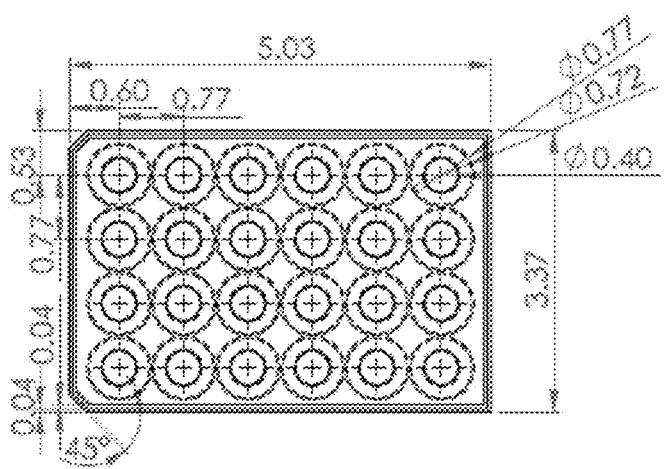
FIG. 9A
FIG. 9B
FIG. 9C
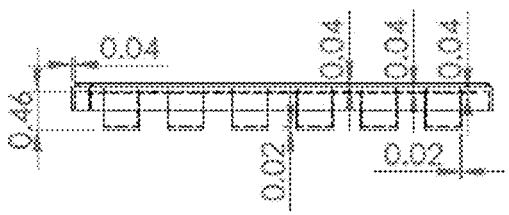

FIG. 12A

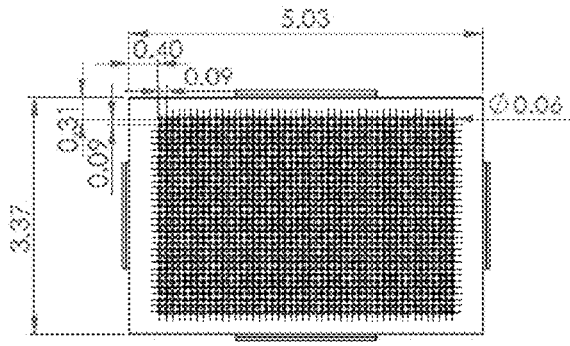

FIG. 12B

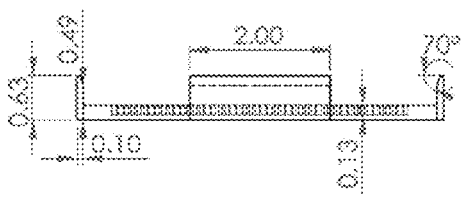

FIG. 12C

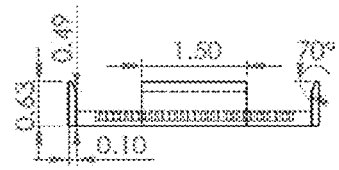

FIGURE 13

| Name | Details | Wt (oz) | Material | Magnetization direction | Pull Force (lbs) | Surface Field (Gauss) | Brmax (Gauss) | Bhmax (MGOe) | Grade |
|---|---|---|---|---|---|---|---|---|---|
| MagPen | 0.125x1.5 inches N42 Cylinder | 0.0798 | NdFeB | Axial | 0.91 | 6594 | 13200 | 42 | N42 |
| Single Well | 0.75 inches N42 Mounting Magnet | 0.374 | NdFeB | Axial | 19.71 | N/A | 13200 | 42 | N42 |
| 6 Well | 1.25 inches N42 Mounting Magnet | 1.63 | NdFeB | Axial | 58.27 | N/A | 13200 | 42 | N42 |
| 24 Well | 0.25x0.125x0.5625 inches N52 Ring | 0.0894 | NdFeB | Axial | 3.74 | N/A | 14800 | 52 | N52 |
| 96 well Ring | 0.1875x0.0625x0.1875 inches N42 Ring | 0.02 | NdFeB | Axial | 1.85 | N/A | 13200 | 42 | N42 |
| 384 well Ring | 0.125x0.0625x0.25 inches N52 Ring | 0.01 | NdFeB | Axial | 0.84 | N/A | 14800 | 52 | N52 |
| 96 and 384 well cylinder | 0.0625x0.25 inches N52 Cylinder | 0.00333 | NdFeB | Axial | 0.2 | 7343 | 14800 | 52 | N52 |
| 1,536 well cylinder | 1.25x6.35 mm N52 Cylinder | 0.00206 | NdFeB | Axial | 0.19 | 7356 | 14800 | 52 | N52 |

MICROPLATES FOR MAGNETIC 3D CULTURE

PRIOR RELATED APPLICATIONS

This application is a Divisional Application of pending application Ser. No. 14/965,702, filed, Dec. 10, 2015, which is a Continuation-in-Part of application Ser. No. 13/762,103 filed Feb. 7, 2013, published as US20150275165 and US20140220672, Application No. PCT/US2011/046183 filed Aug. 2, 2011 and published as WO2013019212, and 61/372,164, filed Aug. 10, 2010, each incorporated by reference in its entirety for all purposes. It is also a Continuation-in-Part of application Ser. No. 14/331,377 filed Jul. 15, 2014 and published as US20140322784, application Ser. No. 13/070,873 (now U.S. Pat. No. 8,815,231, issued Aug. 26, 2014), Application No. PCT/US2009/058473 filed Sep. 29, 2009 and published as WO2010036957, and 61/099,966, filed Sep. 25, 2008, each incorporated by reference in its entirety for all purposes.

FIELD OF THE INVENTION

The invention relates to various devices for manipulating magnetic cells that have magnetic particles in them or attached to them, which is important in biological research and applications. More particularly, the invention relates to simple, durable and inexpensive vessels for culturing and bioprinting magnetic cells, and method of making or using same.

BACKGROUND OF THE INVENTION

Cell culturing, which is the growth of cells in an artificial in vitro environment, is a crucial technique in life science research and development and many biotechnology and health applications. An ideal cell culturing environment is one that promotes fast and robust growth of healthy cells, wherein the cell morphology and function are dominated by cell-cell interactions with cells of the same or different type, cell-specific signaling, and/or experimental control variables, rather than being influenced by the properties of the artificial culturing environment. Often, it is desirable to grow cells that closely resemble cells grown in living organisms, including their gene expression, functional characteristics of differentiated cells, morphology, distribution and organization, and the formation of an extracellular matrix. Cost and scalability of production are also critical considerations for the application potential of such technologies.

As interest in nanotechnology, materials, and cellular biology has grown, it has become evident that an important limitation in our ability to manipulate, print or bioprint, grow and use cells and tissues has been our lack of ability to control the pattern and organization of cells and tissues useful for cellular biology and medicine.

During development of living organisms, structure and order in the form of patterns naturally emerge through mechanisms that are still not fully understood. If one wants to study or replicate living tissue in an artificial environment, it is critical to be able to reproduce the naturally existing patterns and chemical and mechanical environments as closely as possible. The ability to engineer and control the patterns of cells and forces present within living tissue, especially in three-dimensions and/or on surfaces, will enable many bioengineering and medical applications heretofore not realized.

Traditional cell culturing in Petri dishes produces two-dimensional (2D) cell growth with gene expression, signaling, mechanical environment, and morphology that can differ significantly from conditions in 3D living organisms, and thus compromising the clinical relevancy of the cells or tissue for medical use.

While rotating bioreactors or protein-based gel environments have been developed in attempts to allow three-dimensional (3D) cell culturing, broad application of such methods has been severely hampered by high-cost or complexity. Thus, a platform technology to enable 3D cell culturing is still an unmet need.

Furthermore, as the use of cultured cells continue to develop, it is increasingly difficult to develop systems for safely manipulating and handling these entities. For example, regulatory agencies and good laboratory practices often attempt to minimize the amount of exposure of cells to external objects, so as to minimize contamination. Thus, devices which can manipulate cells and tissue without exposure to external environment are desirable.

A recent development in 3D cell culturing techniques is to use magnetic forces on cells (magnetized with nanoparticles) or on magnetic microcarriers coated with cells, to create three dimensional cell cultures (e.g., Akira in US2006063252, WO2004083412, WO2004083416; Becker in US2009137018, WO2005003332; Felder in US2005054101, WO2005010162; Souza in WO2010036957; Ito, et al., Medical Application of Functionalized Magnetic Nanoparticles, JOURNAL OF BIOSCIENCE AND BIOENGINEERING 100(1): 1-11 (2005); and Souza, G. R. et al. Three-dimensional Tissue Culture Based on Magnetic Cell Levitation. Nature Nanotechnol. 5, 291-296, doi:10.1038/nnano.2010.23 (2010)).

Ito, et al., Medical Application of Functionalized Magnetic Nanoparticles, Journal of Bioscience and Bioengineering 100(1): 1-11 (2005), and US2006063252, WO2004083412, WO2004083416 merely use a neodymium magnet placed outside the bottom of the well. Like the magnet on a lid, these are not amenable to scale up, are easily dislodged, and do not allow for complex manipulations of culture conditions.

US2005054101 and WO2005010162 describe a machine for holding and moving magnets to move, position, and agitate magnetic microcarriers and attached cells. However, this device is not compatible with microscopy tools, and it requires a stand-alone complex device. Neither does it provide easy access to the levitated or magnetically bioprinted cultures, thus making it difficult to manipulate the cultures. Furthermore, cells have to be first attached to the surface of microcarriers, which are several times larger than a single cell. This introduces an artificial substrate with which cells interact, rather than rapidly promoting natural cell-cell interactions. The magnetic fields and field gradients produced by this arrangement are also relatively weak and require cells to be attached to large microcarriers containing a large amount of magnetic material in order to manipulate them.

US2009137018 and WO2005003332 described a static arrangement of magnets for levitation of microcarriers. This device is cumbersome however, and not suitable for scale up. Also, this device requires cells to be placed in a bag and a large magnet is above or around the large plastic bag. Thus, the device is not compatible with microscopy tools. Neither does it provide easy access to the levitated cultures, making it difficult to manipulate the cultures. Furthermore, again the cells are first attached to the surface of the microcarriers, which as discussed above introduces an artificial substrate into the culture. The magnetic fields and field gradients produced by this arrangement are also relatively weak and require cells to be attached to large microcarriers containing a large amount of magnetic material in order to manipulate them.

To make 3D cell culturing with magnetic forces more convenient, flexible, and safer for users, there is a great need for improving the methods and hardware to hold magnets in the proper orientation with respect to the cells and container in which they are contained. There is also a great need for methods and hardware for manipulating the magnets and cells during and after culturing. In many cases it would be advantageous to have such systems be compatible with commonly used cell culturing vessels like flasks and Petri dishes, multi-well plates, and high-throughput culturing systems.

There is also great need to easily apply the magnetic field in order to keep the cultures under a constant magnetic field. Applying a variable or constant force (here by means of magnetic field impinging onto the magnetic nanoparticles) and providing minimum disturbance in the culturing media and culture position is desirable. Furthermore, if one would want to co-culture different cell types temporally and/or spatially, precise control over the magnetic field is needed.

The prior state of the art in magnetic culturing devices was the simple magnet on top of a Petri dish used by Souza in WO2010036957 and Souza, et al. Three-dimensional Tissue Culture Based on Magnetic Cell Levitation. *Nature Nanotechnol.* 5, 291-296, doi:10.1038/nnano.2010.23 (2010). While, simple and at least effective in principle, such devices are not amenable to scale up, are easily dislodged, and do not allow for complex manipulations of culture conditions or magnetic cells.

US20150275165, US20140220672, WO2013019212, and 61/372,164, filed Aug. 10, 2010, by the same inventor herein, each describe hardware specifically designed for 3D culture of magnetized cells. Those applications claim a culture plate with a lid having depressions therein into which magnets are snap fit, screwed on, adhered or otherwise attached. Thus, the magnet is firmly held and cannot be accidentally dislodged. However, such devices are subject to continual improvement, and this application provides or of more of such improvements.

SUMMARY OF THE INVENTION

The present invention relates to devices for holding magnets in a proper orientation with respect to vessels for 3D cell culturing or co-culture wherein at least one of the cell types being co-cultures is magnetized, either as a component of the vessel, or a separate component working with the vessel. The present invention also relates to magnetic pipettes for manipulating those magnetic cells.

Any cell types or combinations of cells types can be used herein, including without limit immune cells, circulating tumor cell (CTC), non-adhering cells, stem cells, hematopoietic cells, fibroblasts, mesenchyme cells, epithelial, endothelial, astrocyte, muscle, interstitial, progenitor cells, etc.

As used herein "vessel" or "well" refers to any container for culturing cells, such as a Petri dish, flask, microfluidic chips, microfluidic devices, multiwell culturing plate, test tubes, and the like. Although standard microtiter plates are currently preferred, it is expected that the art will migrate to a microfluidic device in the future as such devices become more robust and standardized and handling equipment for same becomes ubiquitous.

By "over said well", we mean that the magnet cannot dip into the culture media when the magnet is in use, but sits over the culture media. The device can also sit under the entire plate, wherein, in this orientation, the media is not contacted either.

By "microplate" or "microtitre plate" or "multiwell" plate or vessel what is the industry standard microplate. Note that ANSI-SLAS publishes standard sizes for microtitre plates in order to ensure interoperability to robotics and multi-pipettors, and these can be found at slas.org/resources/information/industry-standards/.

"Magnet" refers to any material creating a magnetic field and field shape and can be a permanent magnet or an electromagnet.

As used herein, a "magnetic driver" is a lid or cover or bottom that can fit over or under a culture plate and has magnets permanently or reversible affixed thereto, such that magnetic driver can be used with the plate to levitate and/or pattern/print cells being cultured in the plate.

Reference to the "under" surface of a cap is with respect to the lip, the under surface having a lip or edge on the same side.

The devices described herein are designed to position magnets at an appropriate distance from cells and from neighboring magnets (when neighboring magnets are present) to create the necessary magnetic field profiles to levitate and/or manipulate cells and to hold the magnets in place during use. The devices also improve safety and ease of use of magnets by keeping them aligned and keeping them from colliding with each other. Preferably, the devices are used under the plates, thus not impeding cell access.

Capabilities to move the magnets are incorporated into the design in some realizations of the invention, which enable the directed manipulation of tissue grown from cells containing or attached to magnetic material. Thus, in some embodiments the height of the magnets and horizontal position of the magnets on cell culture vessels is easily adjusted. In some cases, the devices of the invention are designed to be compatible with commonly used cell culturing vessels like Petri dishes, multiwell plates, microfluidic chip or device, and high-throughput culturing systems.

Preferably the magnet is a permanent magnet and has a field strength of about 0.00005-2 Tesla, preferably 0.005-1.5 T or about 0.5-1 T (one tesla is equal to 10,000 gauss). However, the strength is inversely proportional to the cube of the distance from the magnetic source, and thus the required field strength can vary depending upon the distance from magnet to the cell culture. In those embodiments where multiple magnets are used in arrays, there will be some interaction with neighboring magnetic fields, and thus optimization of placement, size, strength, etc. is needed for the application and cell type.

The magnet can be any shape or combination of different magnets and/or electromagnets to form a pattern needed to affect the required cell assembly or growth patterns. For example, it may be possible to grow tubes, useful for example in growing veins and arteries, with a washer-shaped or annular ring magnet that establishes a magnetic field with a hole in the center. Spheres of cells are possible with many magnet shapes, including disks.

Preferably, a rare earth magnet is employed, but electromagnets could also be used. Examples of rare earth magnets suitable for use with the present invention include, but are not limited to, neodymium rare earth magnets, samarium-cobalt rare earth magnets, $Nd_2Fe_{14}B$, $SmCo_5$, $Sm(Co,Fe,Cu,Zr)_7$, $YCO_5$, or any combination thereof.

Neodymium rare earth magnets are the strongest and most affordable type of permanent magnet, and are generally preferred, but samarium-cobalt magnets have a higher Curie temperature (the temperature at which the material loses its magnetism) and may be preferred for uses involving high sterilization temperatures.

Particular types of rare earth magnets may also be selected as desired according to the conditions to which the rare earth magnets may be exposed. For example, any of the following factors may be considered in selecting a type of rare earth magnet: remanence (Br) (which measures the strength of the magnetic field), coercivity (Hci) (the material's resistance to becoming demagnetized), energy product (BHmax) (the density of magnetic energy), and the Curie temperature (Tc). Generally, rare earth magnets have higher remanence, much higher coercivity and energy product than other types of magnets. Where high magnetic anisotropy is desired, $YCO_5$ may be suitable for use In place of or in addition to the rare earth magnets, powered magnets may be incorporated into the devices of the invention, and batteries may be used to power the powered magnets as desired. Alternatively, RF or other electromagnetic radiation activated power sources can be used to power the magnet, such as is used with RFID tags. However, for simplicity, durability, and cost reasons, the permanent magnet is preferred, especially the neodymium rare earth magnets.

We have tested a number of magnets, both in modeling studies and in real experiments, and can elaborate a number of principals for the selection of magnetic size, strength and shape.

Firstly, the magnet size is confined by the size of the plates with which it will be used, as excess magnet is a waste of resources.

Second, the height of the magnet can vary with increasing field strength, stronger magnets being held farther away than weak magnets, and generally the magnets being positioned so as to not touch the media or an intervening cover (if used). These considerations must be balanced against the magnet's lifting height of the magnet (how far away the magnet can be and still lift cells), as well as the desired growing height. Magnetic field interference is also important in designing multi-magnet holders, and it is generally preferred that the magnets of multiwell plates be positioned so as to alternate polarity (North (+) and South (−)) in adjacent magnets. Additionally, meniscus effects from the media surface shape become increasingly important in plates with increasing well number.

Third, our results indicate that the gradient and field strength produced by each permanent magnet are important considerations, and that a steep gradient and high field strength serve to minimize interference between magnets and still provide good lifting and growing heights.

Fourth, the shape of the magnet can be varied to influence the shape and size of the growing 3D culture. Next, the position and polarity orientation of a combination of magnets can be varied to influence the shape and size of the growing 3D culture. For example, annular magnets can lead to annular cultures (that can be stacked to form tubes), and long magnets can lead to 3D cultures that are longer than wide.

We have now also found that in preparing multiwell plates it is important to assemble to insert the magnets in alternating fashion. Otherwise, the fields repel making assembly difficult. Furthermore, the dimensions and strengths have been optimized for various multiwell plates.

We tested candidate magnets for a 35 mm plate that included various disc magnets from K&J MAGNETICS®. Magnet MM-A-32 and MINI-A-20 resulted in desirable levitation results when used for 35 mm petri plates. MM-A-32 is an annular shaped magnet of 1.26" (32 mm)×0.32" (8 mm) with a small tapered countersunk central hole 0.22-0.39". It is a Grade 38 NdFeB magnet with Ni—Cu—Ni coating, axial poles, a pull force of 55.1 lbs, Br max of 12,600 Gauss and BH max of 38 MGOe. MM-A-20 is very similar, 0.79"×0.28", hole 0.18-0.33", but due to its smaller size having a pull force of only 13.20 lbs, Br max of 12,600 Gauss, and BH max of 38 MGOe. The same magnets can be used for a standard six well plate (127.76 mm×85.47 mm, wells are 35.43 mm×17.4 mm).

D42-N52, D46-N52, D48-N52 resulted in desirable levitation for a 24 well plate.

We also tested candidate magnets for a typical 96 well plate that includes D22-N52, D23, and D24-N50 from K&J MAGNETICS®. In our experiments, we found that D22-N52 has the steepest gradient and produces forces comparable to MM-A-20 and MM-A-32 and is a good choice for a 96 well magnet holder. D22-N52 is a disc shape magnet (no hole) of 1/8×1/8 inches, and has a pull force of 0.84-1.05 lbs. The surface field is 6619 Gauss, the Br max is 14,800 Gauss, and the BH max is 52 MGOe.

The invention includes any one or more of the following embodiments, in any combination(s) thereof:

A magnetic culture plate, comprising:
a)  a cell culture vessel and a cap for said vessel,
b)  said cap having a lip around an outer circumference thereof and being shaped to fit over or under said cell culture vessel,
c)  said cap having a depression into which a magnet is affixed, thus holding said magnet over said culture vessel when said cap is in place over said vessel.

A multiwell cell culture vessel, comprising a vessel having plurality of wells in an array, a cap covering vessel and said plurality of wells, said cap having a plurality of magnets in an array, each magnet affixed to a depression in said cap or on a post on said cap, such that each of said wells has a magnet over said well when said cap is in place over said vessel, preferably each adjacent magnet being affixed in opposite polarity.

A magnetic cap for a microplate, comprising a cap sized to cover a standard ANSI-SLAS microplate having a plurality of wells in an array, said cap having lip around a circumference thereof and a plurality of magnets in an array, each magnet affixed to a depression in said cap or on a post on said cap, such that each magnet sits over a well when said cap is in place over or under said microplate and such that each adjacent each adjacent magnet is affixed in opposite polarity.

A magnetic culture plate or cap as herein described, wherein said vessel has a plurality of wells, and said cap has a plurality of depressions, in each of which a magnet is affixed, such that every magnet is orientated in an opposite orientation to an adjacent magnet.

A magnetic culture plate or magnetic cap as herein described, said magnet being adhered to a bottom of said depression, or snap fit into said depression, or friction fit into said depression.

-continued

Alternatively, the magnet can be a ring magnet affixed over a post.
A magnetic culture plate as herein described, said cell culture vessel being an ANSI-SLAS standard microtiter plate having 6 wells and 6 magnets of 20-100 lbs pull force, 10000-15000 Gauss $Br_{max}$ and 30-60 MGOe $Bh_{max}$; or having 12 wells and 12 magnets of 2-20 lbs pull force, 10000-15000 Gauss $Br_{max}$ and 30-60 MGOe $Bh_{max}$; or having 24 wells and 24 magnets of 2-10 lbs pull force, 10000-15000 Gauss $Br_{max}$ and 30-60 MGOe $Bh_{max}$; or having 96 wells and 96 magnets of 0.5-2 lbs pull force, 10000-15000 Gauss $Br_{max}$ and 30-60 MGOe $Bh_{max}$; or having 384 wells and 384 magnets of 0.5-1 lbs pull force, 10000-15000 Gauss $Br_{max}$ and 30-60 MGOe $Bh_{max}$.
A magnetic cap as herein described, said cap fitting over or under an ANSI-SLAS standard microtiter plate and said cap having 6 magnets of 20-100 lbs pull force, 10000-15000 Gauss $Br_{max}$ and 30-60 MGOe $Bh_{max}$; or having 12 magnets of 2-20 lbs pull force, 10000-15000 Gauss $Br_{max}$ and 30-60 MGOe $Bh_{max}$; or having 24 magnets of 2-10 lbs pull force, 10000-15000 Gauss $Br_{max}$ and 30-60 MGOe $Bh_{max}$; or having 96 magnets of 0.5-2 lbs pull force, 10000-15000 Gauss $Br_{max}$ and 30-60 MGOe $Bh_{max}$; or having 384 magnets of 0.5-1 lbs pull force, 10000-15000 Gauss $Br_{max}$ and 30-60 MGOa $Bh_{max}$.
A magnetic cap as herein described, having the dimensions of FIG. 7, 8, 9, 10, 11 or 12 or having the dimensions and strengths of FIG. 13, or both.
A method of making a magnetic driver for a standard microtiter plate, said method comprising:
a) obtaining a cap having a circumferential lip that fits both over and under a separate microtiter plate having a plurality of wells; and
b) affixing a plurality of magnets to said cap such that every well has a magnet over said well when said cap is in place over or under said microtiter plate, and such that every magnet has a polarity opposite each adjacent magnet.
A method of making a magnetic driver as herein described, wherein said affixing step is snap-fitting each magnet to a depression in an upper surface of said cap or adhering each magnet to a depression in an upper surface of said cap, or fitting a ring magnet over a post on an upper surface of said cap or fitting a ring magnet over a post on an under surface of said cap.
A method of 3D cell culture, comprising:
a) incubating one or more cell types in a solution of iron oxide nanoparticles until said cell types contain about 30-150 pg/cell of iron oxide;
b) suspending said cell types containing said iron oxide in a culture medium;
c) aliquoting samples of said suspended cell types to one or more wells of a multiwell plate;
d) placing the magnetic cap of claim 13 above or below said multiwell plate; and
e) incubating said multiwell plate until a 3D culture of cells is formed.

BRIEF DESCRIPTION OF THE DRAWINGS

FIG. 1A. Exploded view of single-well magnet drive with magnet and culture plate and lid.

FIG. 1B. Assembled magnet drive in place under a typical petri plate.

FIG. 1C. Three single well plates in a row showing the intra-magnet distance -l-.

FIG. 7A-C. Top (7A), long side (7B) and short side or end (7C) views of a 6 well cover with dimensions given. Side rims do not completely circumnavigate the magnetic drive, but a portion of a vertical rim on each side keeps the driver centered over the plate. Six magnets (not shown) fit into the wells or depressions provided for same (see dotted line in side views) such that each magnet is oriented with the opposite polarity to its neighbors.

FIG. 9A-C. Top (9A), long side (9B) and short side (9C) views of a 24 well cover with dimensions given. This variation lacks the side edges or rims and fits under the plate.

FIG. 12A-C. Top (12A), long side (12B) and short side (12C) views of a 1536 well cover with dimensions given.

FIG. 13. Preferred magnets used with the magnetic drives of FIG. 7-12. A small degree of tolerance in size is permitted, providing the magnets till fit into the wells on the magnetic drive. $Br_{Max}$ for each magnet varies from about 13000 to 15000 Gauss, $Bh_{Max}$ varies from about 40 to 55 MGOe.

DETAILED DESCRIPTION

Figure 1D:
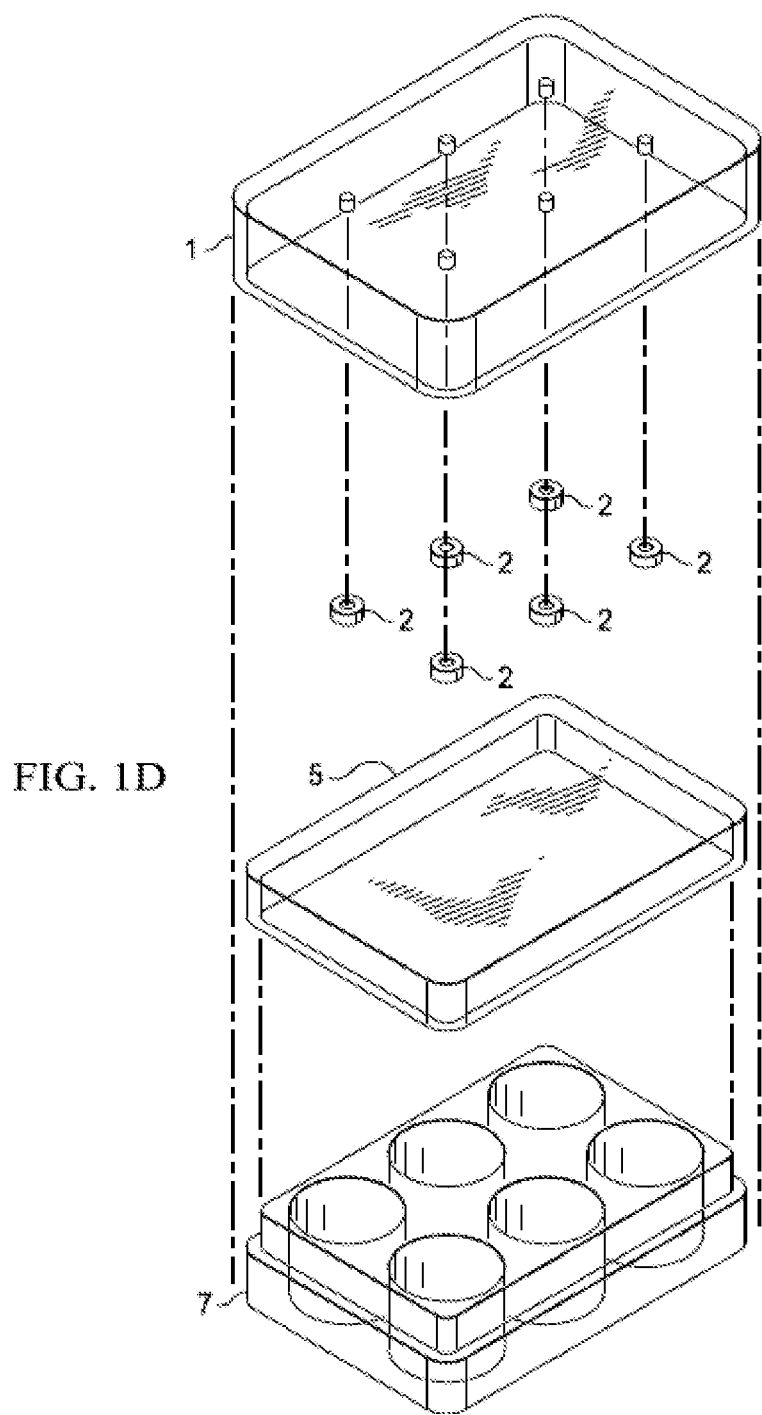
FIG. 1D. A six well magnet holder and standard 6 well plate.

Generally speaking the invention relates to a magnetic cell culture plate comprising at least one well having a matching cap fitting over (or under) said well, at least one of said well or said cap being having a magnet affixed to said well or cap. Alternatively, the invention can comprise just the cap with attached magnet, herein called a magnetic cap or holder or drive, which is sized to fit a culture vessel. Generally, the magnet is affixed to said cap with adhesives, fasteners or is snap fit or friction fit with a receptacle designed to accept a magnet, such as a snap fit receptacle. It is preferred however, that adhesives are used to accommodate a range of usage temperatures.

The magnetic cap can be used either above or below the vessel, and if used above can lie either over the normal vessel cover or if sterilized and without apertures can replace the cover. Preferably, the magnetic cap is used under the plate, and the plate and its cover can be separate devices.

In preferred embodiments, the magnetic cap is adjustable so as to adjust the height of said magnet from the vessel. In other embodiments, the position of the magnet on the cap is also adjustable. In one embodiment, the magnetic cap has an adjustable collar that fits outside or inside the cap and which is fitted with grooves or ridges that match ridges or grooves on the magnetic cap, so that unscrewing the collar has the effect of increasing the height of the magnetic cap. Instead of using a collar, the magnetic cap can also be fitted with screws or other protrusions that can be lengthened, thus having the same effect. This would allow even a square cap to be easily adjustable.

The magnetic cap can also be sized and shaped to fit a multiwell plate. Thus, the invention can comprise a magnetic cell culture plate, comprising a plurality of wells in an array (these wells could be connected by microfluidic channels), a cap covering said plurality of wells, and a plurality of magnets in an array affixed to said cap, such that each well, or each well in a subset of the wells, has a magnet over said well when said cap is in place over or under said plurality of wells. As above, the invention can comprise just the magnetic cap and magnets, which can be used with commercially available plate ware, and the cap height can be adjustable.

In some embodiments, the magnetic cap is merely a plate cover with holes drilled or injection molded therein over each well, and a separate plate having magnetic pins is provided to fit to the cap, the magnets protruding through the hole to varying degrees. In this embodiment, a number of separate plates with magnetic of different lengths or strengths can be provided, again providing the user with an easily customizable magnetic 3D culture hardware. As above, this plate cap can be used above or below a cell culture vessel.

In yet another embodiment, the magnetic cap or magnetic drive has a lip (or rim or vertical edge) to prevent it from being easily dislodged from the plate or plate cover, and has depressions thereon to receive one or more magnets. Preferably, the magnets are snap fit into these depressions, allowing magnets to be switched out for different magnets strengths or shapes. If different magnet shapes are used, the invention can also provide an adaptor for each shape, thus allowing the magnets to be snap fit into the adaptor, and then snap-fit into the drive. In other embodiments, the magnets are more or less permanently affixed, by e.g., an adhesive.

In another embodiment, there is a method of assembling such a multiwell cap or multiwell culture vessel with cap, wherein the magnets are affixed to the cap such that adjacent magnets are in opposite orientation.

Single and Multi-Well Magnetic Hardware

Referring now to the invention in more detail, in FIG. 1A-E and FIG. 2A-C there is shown a magnetic holder that fits on the top or the bottom of a single well cell culture dish. In detail FIG. 1A shows a magnetic holder 1 with a magnet 2 affixed to it. The prototype magnetic holder or drive 1 was made of acrylic, but any polymer, resin, ceramic, glass or metal can be used. Inexpensive polymers such as acrylate or polycarbonate are preferred as durable, inexpensive, sterilizable, and transparent, which allows visualization of contents.

In this instance, the magnetic holder 1 has a hole 9 through which one can visualize the contents of the plate if an annular magnet 2 is used. The magnetic holder 1 can sit over a petri plate 3 with lid or cover 4, or can sit under it, depending on the application and/or magnet orientation.

A circular or disc shaped magnetic drive 1 is shown in FIG. 1, but it could be rectangular, triangular, hexagonal, or any other shape defined by a single or combination of magnets. The preferred shapes are compatible with existing cell culture plates and flasks. We have shown the magnet centered on the cap, but it does not have to be.

The magnetic holder 1 can be used alone, or can be laid over the existing vessel caps 4 as shown herein. An optional aperture 9 can be included in the holder 1 to facilitate imaging the cultures if needed.

The size of this cap will vary depending on the size and shape of the tissue culture vessel and the size and strength of the magnetic field resulting from the magnet being held. As an example, the size of the cap can vary from 5 mm to 100 mm in outer diameter. If this device is to be used to culture large amounts of cells (such as cultures starting with more than 50M cells per vessel), this may require larger magnets, therefore holders could vary in size and shape.

Examples of applications requiring large-scale culture would be the production of recombinant proteins, production of extra-cellular matrix proteins, activation of T-cell by antigen presenting proteins. The height of this cap is a function of magnet strength. Stronger magnets may require taller holders.

The magnet 2 can be cylindrical or disc shaped, ring or washer shaped, square, triangular and the like, but is not limited to these shapes. Here we show a washer shaped magnet 2 with a small hole therein to allow visualization of the culture below.

The size of the magnet will vary according to the application. Example of size is 32 mm in outer diameter and 6 mm in height. This size could very form 2 mm to 100 mm, but the sizes are not limited. A combination of magnets magnetically held together can also be used. For example, magnetic strength can be increased by stacking magnets, such as disk magnets.

FIG. 1B shows the magnet holder 1 assembled with magnet 2 in the center, and in this instance mounted under Petri dish 3, which is covered with the petri cover 4. FIG. 1C shows three such Petri plates 3 side by side, but with magnetic holder 1 on top of the Petri cover 4. The minimum distance -l- between the center of magnet holders is defined by the holder size and magnetic strength of magnets, and should be such that the fields do not unduly interfere.

The magnet 2 can be held in place on the holder 1 with an adhesive or more preferably, the magnetic holder 1 has a fitting into which the magnet 2 can be snap fit. It can also be held in place with any convention fasteners such as screws and the like. Screws or snap fits may be preferred where the magnets 2 are expected to be exchangeable and thus allow easy variation of shape, size and strength.

The magnetic holder 1 also keeps the magnet from random displacement relative to the tissue culture dish due to the lip or edge 6, which fits over the culture plate. In summary, the magnet holder will keep the magnet in place (either on top or at the bottom) relative to the tissue culture flask or Petri plate.

The distance between magnets -l- should be defined relative to the size and shape of the tissue culture flask and/or the strength of the magnet. Stronger magnets will require larger distances to keep neighboring magnets from disturbing their respective levitated cultures and/or interacting with each other in a manner that can cause them to be displaced from the top or bottom of the tissue culture dish. This is also important for safety reasons, to prevent fingers from being trapped between very strong magnets, and avoid cross contamination between samples if magnets are displaced and culture media spilled, and/or sample lost.

The use of the magnetic drive 1 is not limited to top of the culture plates, but it could also be placed at the bottom of well. When at the bottom, the magnet holder provides increased stability and easier access to cells.

FIG. 1D shows a 6 well magnetic holder 1 with six magnets 2 designed to fit over (or under) a six well plate 7 and cover 5. We have shown the magnets 2 here placed underneath the cover, but we have also made a prototype device where the magnets fit into depressions of the surface of the magnetic holder, and where each depression also has a viewing hole. The magnetic holder 1 can have a lip or edge to hold the device in place over a plate as shown here, or can be a flat surface lacking any protruding lip on the underside, as in our first prototype. However, this is less stable and a lip is preferred.

Figure 1E:
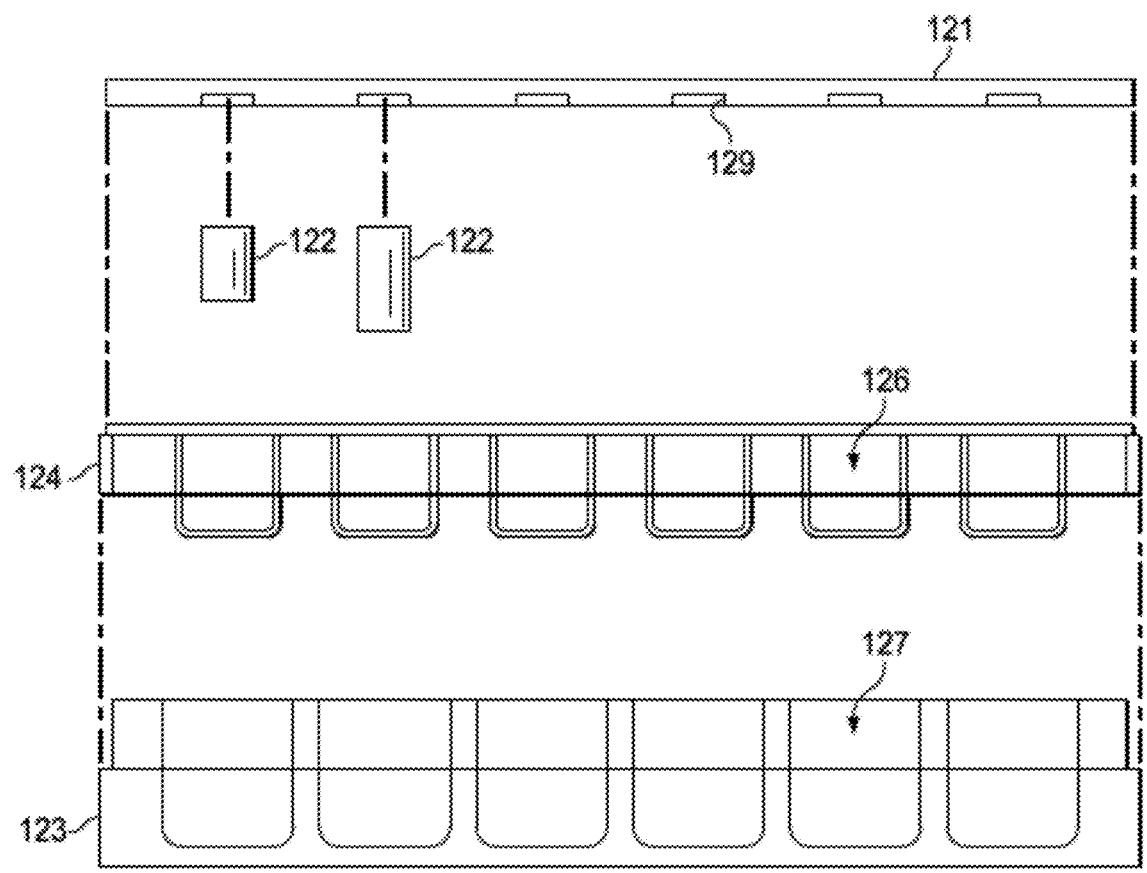
FIG. 1E. 24 well magnet with specially designed lid also having wells designed to fit the magnets and then fit inside the wells of the plate, thus allowing very close positioning of the magnets.

FIG. 1E shows a 24-well plate model wherein both the magnetic drive and a special lid are made to fit either over existing plates or a plate and lid combination will both be made. The magnetic drive 121 will be similar to that already described with magnets 122 placed in an array on the drive or holder 121, which has an array of recesses 129 to receive the magnets 122. Epoxy fixative will then be used to glue 24 ring magnets 122 into the recesses 129 on the drive 121, thus completing levitator assembly and forming the 24-well magnetic drive. This will be used with a culture plate 123 and a specially designed lid 124 having 24 wells 126 fitted to receive the magnets and fit inside the 24 wells of the plate 127. In this way, the magnets can be brought closer to the culture, thus levitating cells, and smaller magnets can be used, thus minimizing interference magnetic fields from neighboring wells. At the same time, the cell cultures are protected from contamination by lid 124. Further, magnet sizes and shapes can easily be switched out by changing holder 121 or the magnets therein.

The special lid can be pre-sterilized and thus preserve the sterility of the system. This will allow the magnet drives to be reusable, while the lid will be disposable or designed for single use. The magnetic drive and special lid concept in FIG. 1E can be adapted with standard or specially designed multiwell plates with 6, 12, 24, 48, 96, 384 and/or 1536 wells.

Figure 2A:
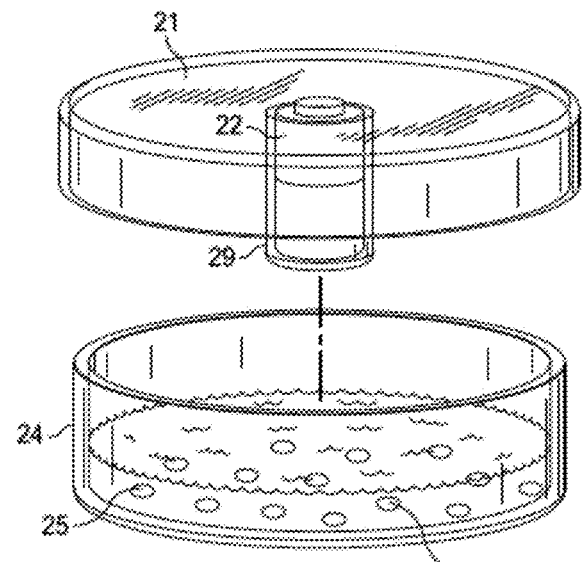
FIG. 2A. Magnet holder cap modified with protruding surface for collecting cells levitating cells.
Figure 2B:
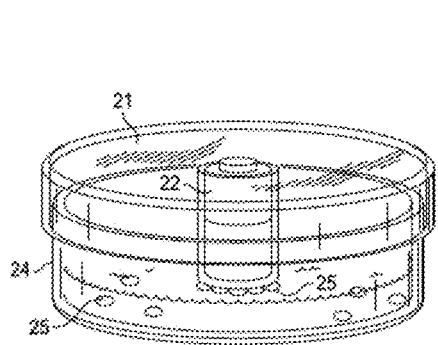
FIG. 2B. The protruding surface can reach the media in the petri plate, thus collecting the cells for transfer, e.g., to another plate.
Figure 2C:
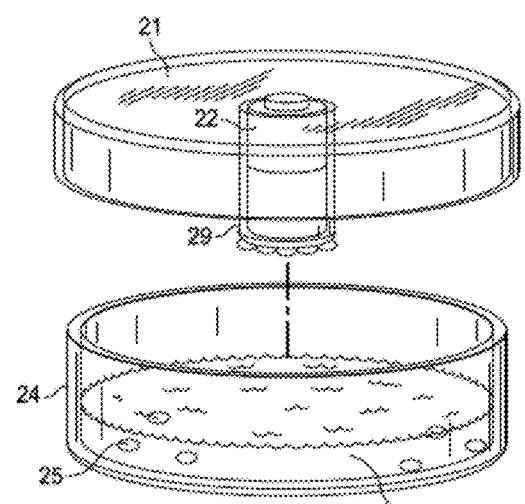
FIG. 2C. Magnet holder cap with protruding surface carrying magnetized cells.

In FIG. 2A there is shown a magnet holder 21 modified with protruding surface 29 for collecting levitating cells. In this embodiment, the magnet is placed inside a cap-shaped protruding surface (but the surface can be any shape), such that only this surface contacts media when in use. Tissue culture vessel 24 is shown with cells 25 on the bottom. In FIG. 2B, the holder is moved close enough to the plate 24 so that cells 25 are collected on the protruding surface 29 by attraction to the magnet 22. Once attached to the immersed surface, the cells can be easily removed from solution as in FIG. 2C. The attached cells can then be counted, separated between levitating and non-levitating cells. The surface attached cells can also be used for analysis, culturing in different flask by displacing the magnet, washing cells off with media or trypsinizing the cells. Furthermore, the device can be used to separate, sort, transfer, and evaluate yield of magnetized cells. It is possible to make this protruding surface snap or pressure fit to a protruding edge (not shown) on the drive, thus allowing single use, pre-sterilized surface to be prepared and snap fit onto the drive when needed, in the same way that a pipette tip if pressed onto a pipettor. In this embodiment, a simple means for ejecting the cap can also be provided.

FIG. 3 and FIG. 4 show multiwell magnet assembly for culturing multiple samples by magnetic levitation. The components of FIG. 3 are a multiwell magnetic drive 31 with an array of magnets 32 protruding therefrom. In more detail, this multiwell magnet holder was made of acrylic or polycarbonate wherein a number of holes were drilled and magnets were inserted therein. In this instance, the magnets were held by either an adhesive or by friction inside a metal holder, heat welding, snap fit, fasteners or any other means can be used to secure the magnets.

The multiwell magnetic holder 31 can be used with standard or specially designed multiwell plates 33 with 6, 12, 24, 48, 96, 384 and/or 1536 wells 34. We have shown magnet protruding down into the wells in the multiwell case, and the magnetic holder 31 is used without a plate cover because at some point, the magnets must get close enough to the cells 35 so as to levitate same, but avoid interference effects between well. In other cases the magnets 32 can be sized so as to not protrude into the well, and the device can be combined with a plate magnet 36, as shown in FIG. 3B. In such case, the magnetic holder 31 could still be used with a plate cover (not shown). Once cells reach the meniscus of the media and the smaller magnets 32 have the strength to sustain levitation, this large plate magnet 36 could be removed.

Figure 3A:
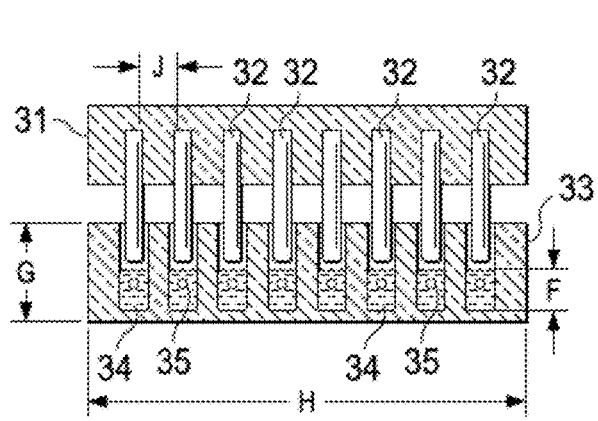
FIG. 3A. Multi-magnet holder for 96 well tissue culture plate. This embodiment is intended to be used with only the bottom of a 96 well plate (not the cover), allowing the magnets to get closer to the cells.
Figure 3B:
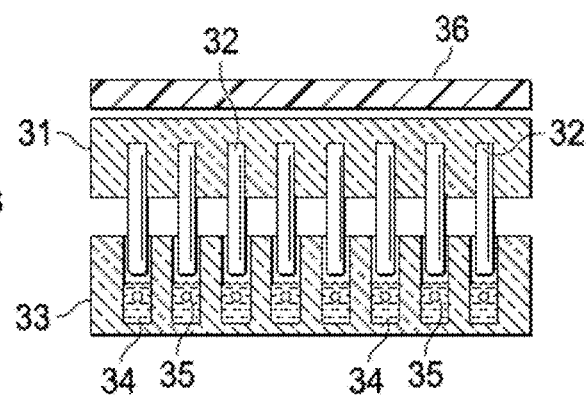
FIG. 3B. Same plate as FIG. 3A, but with an additional plate magnet placed on top to further increase field strength. In such an embodiment, the plate could be used with its cover (not shown) because of the extra field strength provided by the plate magnet.

Also shown in FIG. 3A is -G-, which is the height of the microwell plate 33. This height will vary depending on the application and/or magnetic strength of magnets being used. Shorter plates of approximately 2.5 mm in height, but not limited to it, would be optimum for higher throughput applications, such as when using 96, 384, and 1536 plates. The length of multiwell plate is -H- and the depth of the media is -F-.

Magnets may protrude inside each well to get close enough to the cells to provide the needed magnetic field to levitate cells. With stronger magnets, the magnet can be completely above the wells, and even above the sterile well cover or lid. In some embodiments, these devices could consist of 6, 12, 24, 48, 96, 384, 1536 magnets, or any number in between.

Figure 4A:
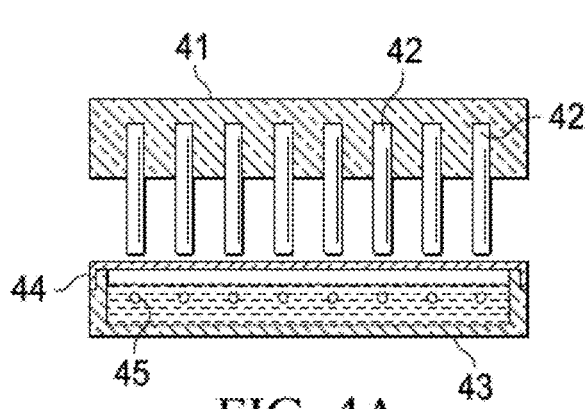
FIG. 4A. Multi-magnet holder for culturing vessel without individual wells (or with one large well). The magnets can either penetrate into the plate, as shown in FIG. 3A-B, or not as shown here, depending on field strength. Preferably, the magnets do not touch the media.
Figure 4B:
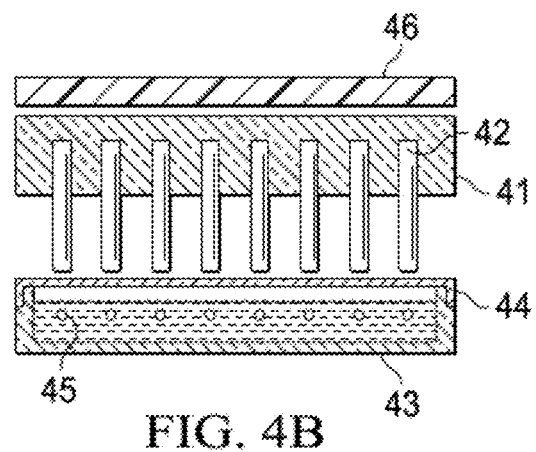
FIG. 4B. An additional plate magnet.

The magnetic holder described in FIG. 3A-B does not have to be used with plates having multiwells, but can be used with fewer wells or even a single well as shown in FIG. 4A-C wherein the magnetic holder 41 with magnets 42 is used for a large Petri plate or culture dish 43 with lid 44 to levitate cells 45. If needed, the device can also be used with a plate magnet 46 to increase field strength. Magnets 42 can also be removed as needed to fit, e.g., a six well plate. Thus, the device is not limited in use to a plate having the same number of wells as there are magnets.

The magnet holder 41 with magnets 42 described in FIG. 4 could also be placed under the culture dish. Here, cells will be held magnetically at the bottom of the tissue culture dish, allowing them to be printed into different shapes, and depending on the properties of the tissue culture dishes surface (cell-adhering or non-adhering). Thus, in a typical embodiment, the magnetic holder is sized and shaped so as to fit either above or below the vessel, holding the magnets at a fixed distance D from the culture media, wherein D is >0 and is preferably about 0.2-10 mm.

The spacing between magnets will initiate/generate individual levitating cultures, which are held in place and separated by the magnetic field. Therefore, this well-less format can be envisioned as an invisible boundary defined by the magnetic field, without internal mechanical barriers, such as found in a multiwell plates. Once the individual cultures grow, they may come in contact with each other, which could be a desirable feature for creating larger cultures with improved nutrient flow because of the spacing between individual cultures. This could also be used to generate multiple spheroid bodies within the same culture media.

We have obtained proof of principle of such a technique based on label-free monitoring of cells cultured with a prototype 6 well magnetic holder, wherein magnets are held in depressions on the top of a flat piece of plastic, wherein each depression also has a viewing hole drilled therethrough. Using the device was as simple as standard 2D techniques, and it was proven to be faster than any other 3D cell culturing product on the market.

Cells were treated with Nanoshuttle™ (a proprietary solution from Nano3D Biosciences™, Inc. containing magnetic nanoparticles that allows cells to levitate in a magnetic field) and plated into individual wells using media recommended for their specific cell type. The magnetic drive was immediately placed above the culture and magnetic forces gently levitated and guided cells together to quickly induce cell-cell interactions. The cultures were placed in a standard cell culture incubator and, over time, 3D assemblies formed.

The location of the culture assembly can be controlled magnetically. However, the morphology of the assemblies and amount of time needed to reach this stage is cell specific. Some cells types, such as epithelial, form layered sheets and display squamous morphology while others, such as human umbilical vein endothelial cells, display branching structures. Levitated structures can be separated to create multiple samples and viable cells may be removed from the 3D culture for further experimentation. No special additional equipment is required and the magnetic drive is compatible with co-culturing and standard imaging and diagnostic techniques. Cells can be maintained for months and toxins can be introduced into culture and examined for any deleterious effects. Cultures grown with the magnetic drive provide a model of native tissue, which can be exposed to various drugs and monitored for viability.

Figure 5A:
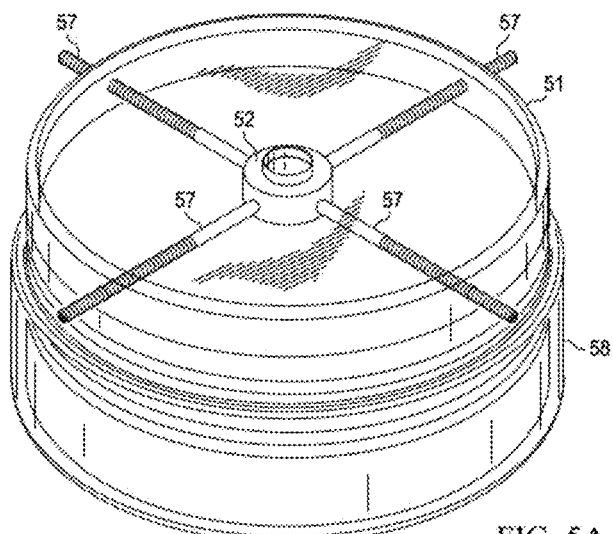
FIG. 5A. Adjustable magnet holders. A. Screws allow the magnet to be adjustable in the horizontal plane. The magnet can either sit on top of the holder or on the under side, provided a lip or edge is provided to hold the magnet in place in the vertical axis, yet allow motion in the lateral or horizontal axis.
Figure 5B:
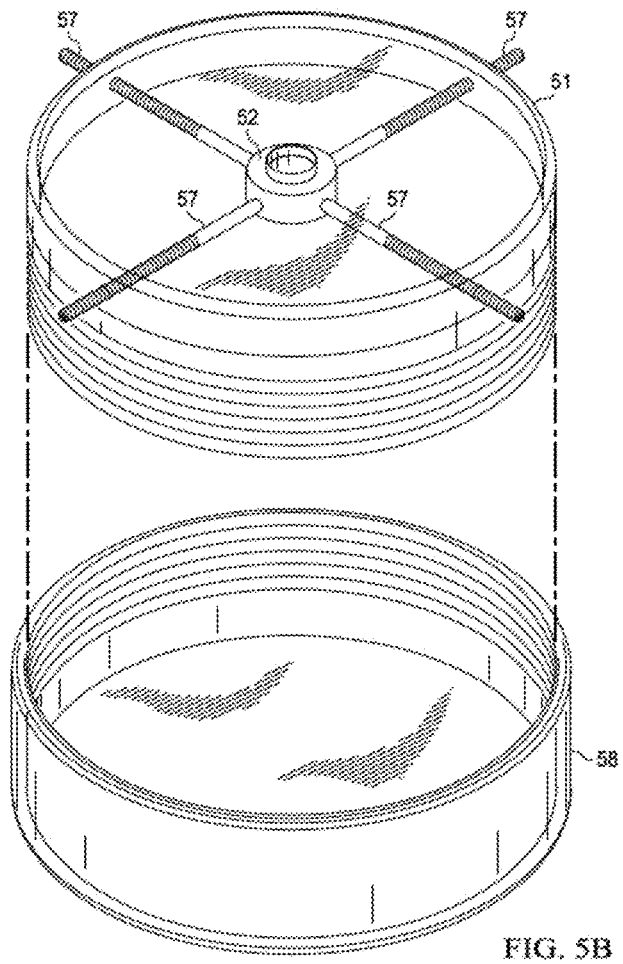
FIG. 5B. A screwable extender allows the magnet to be adjusted in height.

FIG. 5A-B shows the drawings of a holder with adjustable magnet positioning (xyz-axis), such as height, xyz-axis translation (lateral positioning) adjustments of the magnet relative to the tissue culture flask. In detail, the magnetic drive 51 has a magnet 52, and the magnet can be moved around via positioning screws 57. This can also be generalized for a multiwell format and the range of motion may be restricted so that each magnet does not move beyond the range of one well. The height of the magnetic drive can also be adjusted, e.g., by collar 58 with threaded guides for z-axis motion/control.

The xy-axis (horizontal) adjustment may be desirable for translating the magnetized cells sideways. This can be advantageous or useful when cells accumulate under the view path, therefore obstructing a clear image of the levitated cells. This same xy-axis translating action can also be used to disturb the culture.

In FIG. 5A-B, we show a simple mechanical mechanism for displacing the magnet (screw action resulting from threads), however this could be also achieved by electrical (such as, but not limited to, by using solenoids and electric current, electric magnetic), and/magnetic actions. An additional mechanism would be a spring-loaded mechanical actions (similar to a light switch) in which a single mechanical motion raises the magnet. This example can also be used to reduce or remove the magnetic field so the levitated structures fall to the bottom of the culture dish and then can be magnetically raised back up.

One of the applications for removing/reducing the magnetic field would be for higher resolution imaging when it is desirable to have the cells at the bottom of the dish closer to imaging objective or elements, such as in the case of confocal microscopy. In more detail, for multiwell designs, it can work with a lever or other mechanical action instead of a screw. This mechanism is also important for transporting the levitating cultures. When transporting the cultures, if a sudden motion occurs that swings/splashes the media and cells so that the media and cells get too close to the magnet, the magnetic force can pull the cells onto the surface just under the magnet. The cells may then adhere to that surface. By lifting the magnet, it prevents the media and cells from getting close enough to the magnet for them to be attracted to and attached to the surface under the magnet.

Multiwell Magnetic Cap Assembly

When the above multiwell plates were manufactured in bulk, it was discovered that it was quite difficult to assemble the plates when all the magnets were in the same orientation due to the repelling fields. The more wells, the smaller the magnets, and the more difficult assembly became.

Figure 6A:
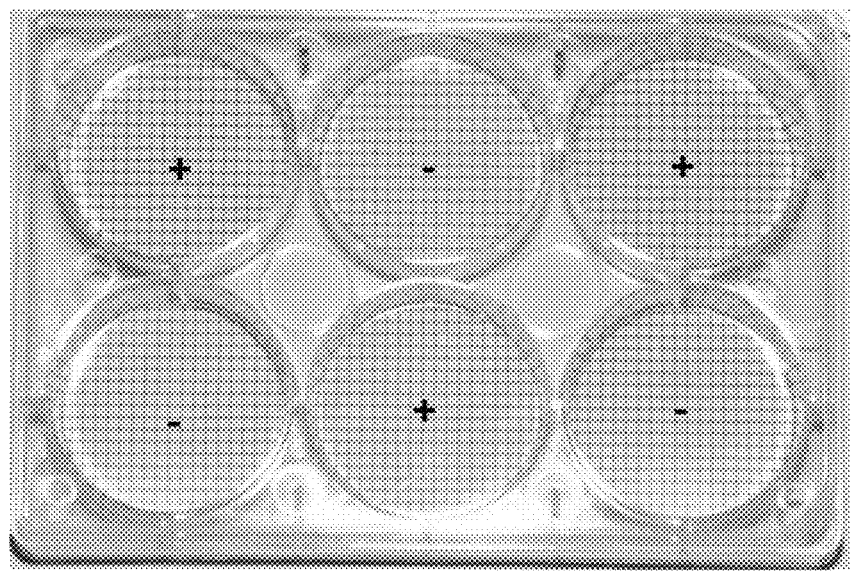
FIG. 6A. Assembly of 6 well plate with alternating magnet orientation or polarity where North is + and South is −. The assembly is easier using alternating magnets, and there is less interference with adjacent magnetic fields.
Figure 6B:
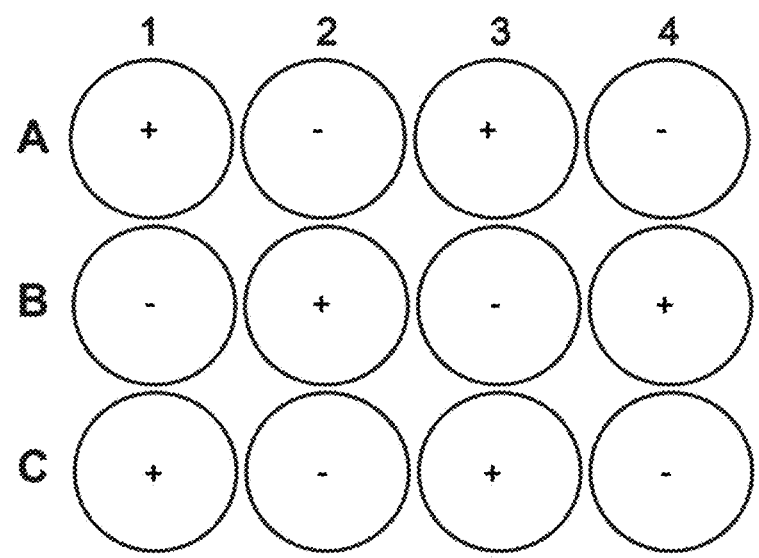
FIG. 6B. Assembly of 12 well plate with alternating magnet polarity.
Figure 8A:
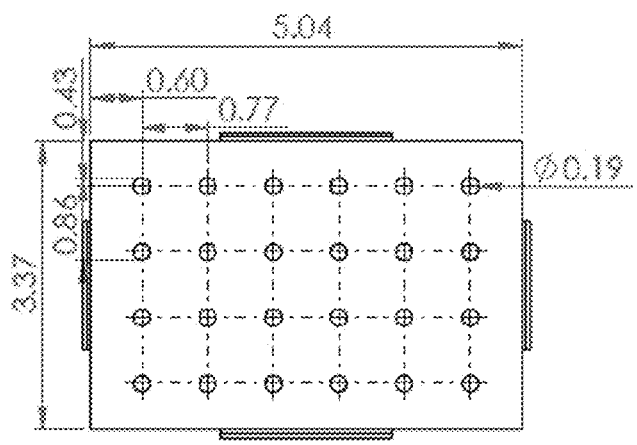
FIG. 8A-C. Top (8A), long side (8B) and short side (8C) views of a 24 well cover with dimensions given.
Figure 8B:
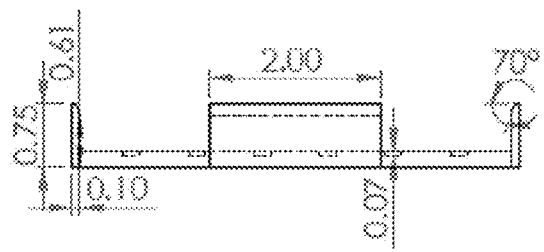
Figure 8C:
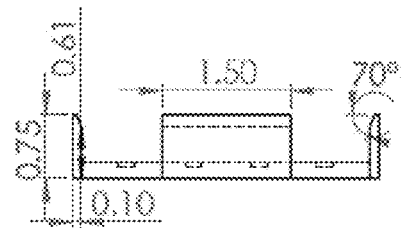
Figure 10A:
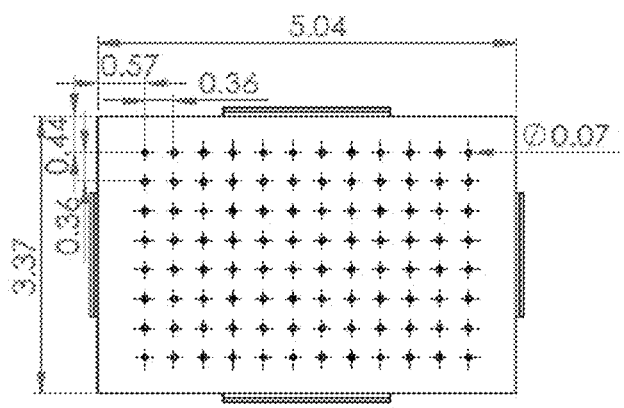
FIG. 10A-C. Top (10A), long side (10B) and short side (10C) views of a 96 well cover with dimensions given.
Figure 10B:
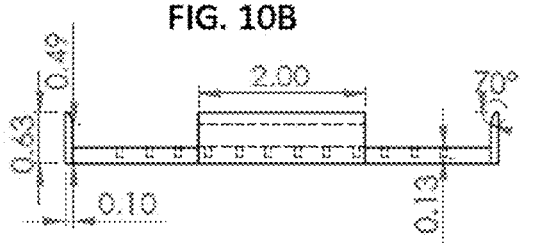
Figure 10C:
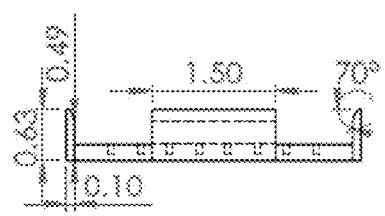
Figure 11A:
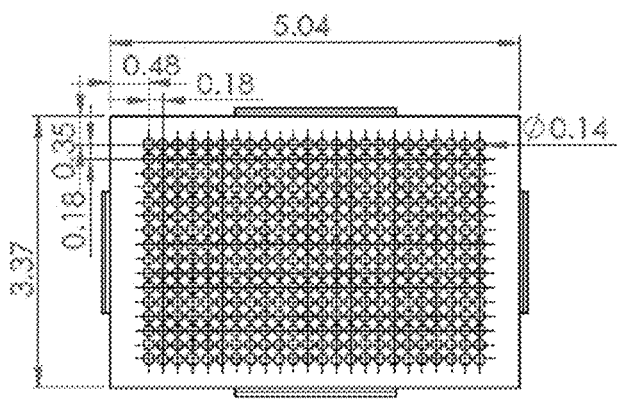
FIG. 11A-C. Top (11A), long side (11B) and short side (11C) views of a 384 well cover with dimensions given.
Figure 11B:
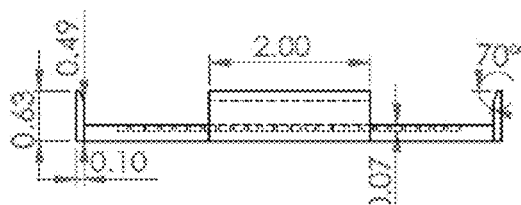
Figure 11C:
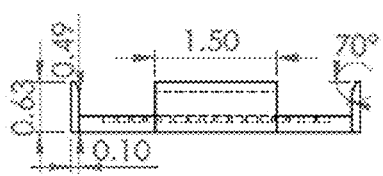

Therefore, we began to assemble the plates with alternating magnets, in the orientations as shown in FIG. 6A and FIG. 6B. It was not clear at first whether such a plate would function as intended, because there was a distinct possibility that there might be destructive interference, opposing fields cancelling each other out. Further, we thought that alternating wells would have cells levitated and repulsed and/or distorted resulting field.

However, our tests showed that the fields do not interfere, and may even show less interference. Further we found that all cells levitated, regardless of orientation (probably because the cells freely rotate in the medium). By contrast, to drive cells to the bottom of the plate (e.g., to make sheets or to change the media), the magnet needed to be under the wells, again regardless of orientation. Therefore, henceforth, all multiwell assemblies were made by inserting magnets in opposite polarity.

Details for 6, 24, 96, 384, and 1536 well magnetic drives are shown in FIG. 7-12, each of which provides a top view (A), and side view (B) along the long side of the drive, and a side view on the short side or end of the drive (C). The magnetic drives are sized to fit over or under a standard microtitre plate. In several of the embodiments, rims are shown. These can traverse the entire length of each side, but need not and herein a rim is shown only at the center third of each cover. These edges or rims along the outside edge of the drive serve to keep the drive centered over the plate, which can be above or below the magnetic drive.

We undertook considerable testing to optimize magnet parameters for the various plates. The results are provided in the Table of FIG. 13. However, a 10-25% variation in strength is certainly possible. The following table provides some useful ranges of strengths.

| Cell culture plate | Pull Force (lbs) | $Br_{max}$ (Gauss) | $Bh_{max}$ (MGOe) |
|---|---|---|---|
| Single Well | 10-100 | 10000-15000 | 30-60 |
| 6 Well | 10-100 | 10000-15000 | 30-60 |
| 24 Well | 2-10 | 10000-15000 | 30-60 |
| 96 well | 0.5-2 | 10000-15000 | 30-60 |
| 384 well | 0.05-1 | 10000-15000 | 30-60 |
| 1,536 well | 0.005-1 | 10000-15000 | 30-60 |

In use, the magnetic drives are used with cell culture plates to levitate cells. First the cells are magnetized, e.g., using NanoShuttle™ (Nano3D BioSciences, TX). NanoShuttle™ is a nanoparticle assembly (~50 nm) consisting of gold, iron oxide, and poly-L-lysine. The poly-L-lysine will non-specifically bind to cell membranes via electrostatic interactions. NanoShuttle™-PL will be retained by the cells for roughly 8 days, after which they are released into the extracellular space. If in 3D, NanoShuttle™-PL will be released into the extracellular matrix, and the 3D culture will retain its magnetic nature. These magnetized cells require magnetic forces (30 pN) only strong enough to aggregate, but not harm cells. Further NanoShuttle™ has been demonstrated to not effect cell proliferation, viability, metabolism, inflammatory or oxidative stress responses, phenotype, and other macro cell functions.

Cells are magnetized by adding NanoShuttle™-PL directly to a flask of cells that is 70-80% confluent, and incubating overnight. Typically, NanoShuttle™-PL is added at a concentration of 1 µL/10,000 cells. The next day, treated cells are enzymatically detached with trypsin and resuspended in suitable media. Cells can also be magnetized in suspension. Briefly, suspension cells are magnetized by mixing them with NanoShuttle™-PL for ~30 min on a gently rotating orbital shaker. The cells are collected, e.g., by centrifugation, resuspended in suitable media and ready for use.

The cells need to take up enough magnetic nanoparticle so as to be levitated in the magnetic field, but not so much as to disrupt the cells normal metabolism. Levels of about 30-150 pg/cell, or about 50 pg of magnetic iron oxide are typical.

Once magnetized, the cells can be levitated for assembly, by adding magnetized cells to a plate, preferably a flat-bottom, ultra-low-attachment plate for maximum levitation efficiency. A magnetic drive as described herein is then placed over or under the cell culture plate. Cell assembly typically begins in minutes, and is complete in hours, although different cell types will require different times, and this is typically optimized before an experiment is begun. If desired, the magnetic drive can be left in place even after the cells have assembled into a stable 3D culture. However, typically the drive is removed and the cells studied further. Typically, the cells retain their 3D structure once stabilized for about 4-8 hrs in the magnetic field.

The above descriptions are illustrative only and not intended to unduly limit the invention as defined by the appended claims.

The following are incorporated by reference herein in its entirety for all purposes:

ANSI SLAS 1-2004 (R2012): Footprint Dimensions
ANSI SLAS 2-2004 (R2012): Height Dimensions
ANSI SLAS 3-2004 (R2012): Bottom Outside Flange Dimensions
ANSI SLAS 4-2004 (R2012): Well Positions
ANSI SLAS 4-2012: Well Bottom Elevation
WO2013019212, US20140220672, and 61/372,164, filed Aug. 10, 2010
US20120171744 U.S. Pat. No. 8,883,471 US20150104844 and 61/245,846, which was filed on Sep. 25, 2009, Materials for magnetizing cells and magnetic manipulation
US20110286975 U.S. Pat. No. 8,815,231, US20140322784 and 61/099,966, filed Sep. 25, 2008, Systems and methods for magnetic guidance and patterning of materials 1. Souza, G. R. et al. Three-dimensional tissue culture based on magnetic cell levitation. *Nat. Nanotechnol.* 5, 291-6 (2010).

2. Tseng, H. et al. Assembly of a three-dimensional multitype bronchiole coculture model using magnetic levitation. *Tissue Eng. Part C. Methods* 19, 665-75 (2013).

3. Tseng, H. et al. A three-dimensional co-culture model of the aortic valve using magnetic levitation. *Acta Biomater.* 10, 173-82 (2014).

4. Castro-Chavez, F., Vickers, K. C., Lee, J. S., Tung, C.-H. & Morrisett, J. D. Effect of lyso-phosphatidylcholine and Schnurri-3 on osteogenic transdifferentiation of vascular smooth muscle cells to calcifying vascular cells in 3D culture. *Biochim. Biophys. Acta* 1830, 3828-34 (2013).

5. Timm, D. M. et al. A high-throughput three-dimensional cell migration assay for toxicity screening with mobile device-based macroscopic image analysis. *Sci. Rep.* 3, 3000 (2013).

The invention claimed is:

1. A magnetic culture plate for three-dimensional (3D) cell culturing, comprising:
   a) a standard ANSI-SLAS microtiter plate comprising a plurality of wells in an array and having a length of 127.76 mm ±0.5 mm and a width of 85.48 mm ±0.5 mm,
   b) a cap comprising a magnetic holder and an intervening cover, wherein said cap is sized to fit over and cover said standard ANSI-SLAS microtiter plate, said cap having a lip around a circumference thereof and a plurality of magnets in an array, each magnet affixed to a depression in said magnetic holder, such that adjacent magnets are oriented in opposite polarity, wherein each magnet of the plurality of magnets protrudes inside a corresponding well of said intervening cover, said intervening cover being arranged between the magnets and the standard ANSI-SLAS microtiter plate and having a number of wells corresponding to a number of magnets of the plurality of magnets, said wells of the intervening cover configured to receive the magnets and to protrude inside the wells of the standard ANSI-SLAS microtiter plate when said cap is fitted in place over said standard ANSI-SLAS microtiter plate, such that each well of the standard ANSI-SLAS microtiter plate has a single magnet protruding inside said well of the standard ANSI-SLAS microtiter plate when said cap is fitted in place over said standard ANSI-SLAS microtiter plate, wherein the magnets do not touch a culture media inside said well, and wherein the cap holds the magnets at a fixed distance of 0.2 to 10 mm from said culture media inside said well of the standard ANSI-SLAS microtiter plate.

2. The magnetic culture plate of claim 1, wherein said magnets are exchangeably affixed to the depression on the cap.

3. The magnetic culture plate of claim 1, said standard ANSI-SLAS microtiter plate having 6 wells and said cap having 6 magnets of 20-100 lbs pull force, 10000-15000 Gauss Brmax and 30-60 MGOe Bhmax.

4. The magnetic culture plate of claim 1, said standard ANSI-SLAS microtiter plate having 12 wells and said cap having 12 magnets of 2-20 lbs pull force, 10000-15000 Gauss Brmax and 30-60 MGOe Bhmax.

5. The magnetic culture plate of claim 1, said standard ANSI-SLAS microtiter plate having 24 wells and said cap having 24 magnets of 2-10 lbs pull force, 10000-15000 Gauss Brmax and 30-60 MGOe Bhmax.

6. The magnetic culture plate of claim 1, said standard ANSI-SLAS microtiter plate having 96 wells and said cap having 96 magnets of 0.5-2 lbs pull force, 10000-15000 Gauss Brmax and 30-60 MGOe Bhmax.

7. The magnetic culture plate of claim 1, said standard ANSI-SLAS microtiter plate having 384 wells and said cap having 384 magnets of 0.05-1 lbs pull force, 10000-15000 Gauss Brmax and 30-60 MGOe Bhmax.

8. The magnetic culture plate of claim 1, said standard ANSI-SLAS microtiter plate having 1536 wells and said cap having 1536 magnets of 0.05-1 lbs pull force, 10000-15000 Gauss Brmax and 30-60 MGOe Bhmax.

9. A method of 3D cell culturing, comprising:
a) incubating one or more cell types in a solution of magnetic nanoparticles until said cell types contain about 30-150 pg/cell of magnetic nanoparticles;
b) suspending said cell types containing said magnetic nanoparticles in a culture medium;
c) aliquoting samples of said suspended cell types to one or more wells of the standard ANSI-SLAS microtiter plate of the magnetic culture plate of claim 1;
d) placing the cap above said standard ANSI-SLAS microtiter plate;
e) incubating said standard ANSI-SLAS microtiter plate until a 3D culture of cells or desired 3D culture printed shape is formed; and
incubating said standard ANSI-SLAS microtiter plate under the influence of a magnetic field for the duration of the 3D culture.

10. The method of claim 9, wherein the magnetic nanoparticles are iron oxide nanoparticles.

* * * * *

UNITED STATES PATENT AND TRADEMARK OFFICE
CERTIFICATE OF CORRECTION

PATENT NO. : 11,932,868 B2
APPLICATION NO. : 17/176188
DATED : March 19, 2024
INVENTOR(S) : Glauco Souza Page 1 of 1

It is certified that error appears in the above-identified patent and that said Letters Patent is hereby corrected as shown below:

On the Title Page

On page 2, Line 10, the filing date of the Continuation application number PCT/US2009/058473 should appear as follows:
--- PCT/US2009/058473, filed Sep. 25, 2009 ---

Signed and Sealed this
Seventh Day of May, 2024

Katherine Kelly Vidal
*Director of the United States Patent and Trademark Office*